United States Patent
Brauer et al.

(10) Patent No.: US 9,702,827 B1
(45) Date of Patent: Jul. 11, 2017

(54) OPTICAL MODE ANALYSIS WITH DESIGN-BASED CARE AREAS

(71) Applicant: KLA-Tencor Corporation, Milpitas, CA (US)

(72) Inventors: Bjorn Brauer, Beaverton, OR (US); Ravikumar Sanapala, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 14/946,604

(22) Filed: Nov. 19, 2015

Related U.S. Application Data (60) Provisional application No. 62/082,141, filed on Nov. 20, 2014.

(51) Int. Cl.
*G01N 21/00* (2006.01)
*G01N 21/88* (2006.01)
*G01N 21/95* (2006.01)

(52) U.S. Cl.
CPC ..... *G01N 21/8851* (2013.01); *G01N 21/9501* (2013.01); *G01N 2201/11* (2013.01)

(58) Field of Classification Search
CPC ... G01N 2021/8854; G01N 2021/8851; G01N 2021/8822; G01N 21/9501; G03F 7/70625; G03F 7/7065
USPC ........... 356/237.1–237.5; 250/307, 310, 311
See application file for complete search history.

(56) References Cited

U.S. PATENT DOCUMENTS

| | | | |
|---|---|---|---|
| 7,570,796 B2 | 8/2009 | Zafar et al. | |
| 7,676,077 B2 | 3/2010 | Kulkarni et al. | |
| 8,041,103 B2 | 10/2011 | Kulkarni et al. | |
| 8,139,843 B2 | 3/2012 | Kulkarni et al. | |
| 8,664,594 B1 | 3/2014 | Jiang et al. | |
| 8,692,204 B2 | 4/2014 | Kojima et al. | |
| 8,698,093 B1 | 4/2014 | Gubbens et al. | |
| 8,716,662 B1 | 5/2014 | MacDonald et al. | |
| 9,518,934 B2 * | 12/2016 | Chen | G01N 21/9501 |
| 2003/0179919 A1 * | 9/2003 | Goldberg | G01N 21/9501 382/141 |
| 2005/0052643 A1 * | 3/2005 | Lange | G01N 21/9501 356/237.1 |
| 2006/0124874 A1 * | 6/2006 | Uto | G01N 21/9501 250/559.45 |
| 2014/0307947 A1 * | 10/2014 | Kurada | G01N 21/95607 382/149 |
| 2015/0324965 A1 * | 11/2015 | Kulkarni | G06T 7/0044 382/144 |

(Continued)

*Primary Examiner* — Hoa Pham
(74) *Attorney, Agent, or Firm* — Ann Marie Mewherter (57) ABSTRACT

Methods and systems for selecting one or more modes of an inspection subsystem or system for inspection of a specimen are provided. The systems described herein are configured to acquire output for all of the modes to be considered at a location of a known defect on the specimen by aligning output, which is generated at the location with a mode known to generate output in which patterned features on the specimen are resolved to a degree that allows the output to be aligned to design data, with the design data for the specimen to identify the location with substantially high accuracy and then without moving the field of view of the inspection subsystem or system from that location, acquiring the output for all other modes. All of the acquired output can then be used to select mode(s) for inspection of the specimen or another specimen of the same type.

20 Claims, 2 Drawing Sheets

(56) References Cited

U.S. PATENT DOCUMENTS

| | | | |
|---|---|---|---|
| 2016/0025648 A1* | 1/2016 | Duffy | G01N 21/8851 356/237.5 |
| 2016/0123898 A1* | 5/2016 | Chen | G01N 21/9501 356/237.5 |
| 2016/0188784 A1* | 6/2016 | Bhattacharyya | G06F 17/5081 716/111 |

* cited by examiner

OPTICAL MODE ANALYSIS WITH DESIGN-BASED CARE AREAS

BACKGROUND OF THE INVENTION

1. Field of the Invention

The present invention generally relates to methods and systems for selecting one or more modes of an inspection subsystem or system for inspection of a specimen.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Many inspection tools have adjustable parameters for many of the output (e.g., image) generation elements of the tools. In this manner, the parameters for one or more elements (such as energy source(s), polarizer(s), lens(es), detector(s), and the like) can be altered depending on the type of specimen being inspected and the characteristics of the defects of interest (DOIs) on the specimen. For example, different types of specimens may have dramatically different characteristics, which can cause the same tool with the same parameters to image the specimens in extremely different ways. In addition, since different types of DOIs can have dramatically different characteristics, inspection system parameters that are suitable for detection of one type of DOI may not be suitable for detection of another type of DOI. Furthermore, different types of specimens can have different noise sources, which can interfere with detection of DOIs on the specimens in different ways.

The development of inspection tools with adjustable parameters has also led to the increasing use of inspection processes that involve scanning the specimen with more than one combination of parameter values (otherwise referred to as "modes") such that different defect types can be detected with different modes. For example, one mode may have a greater sensitivity for detecting one type of defect while another mode may have a greater sensitivity for detecting another type of defect. Therefore, using both modes, an inspection system may be able to detect both types of defects with acceptable sensitivity.

Several currently used methods are available for optical mode selection (OMS), which may be performed to find the best mode for defect inspection. Currently, OMS methods and systems are limited in their ability to assess the best optics mode with design-based care areas (CAs) and design-based accuracy since every mode needs to have design-based alignment and runtime context mapping performed, which is time consuming, risky, and could potentially fail.

In particular, one disadvantage of currently used methods is that design-based accuracy for CAs can only be used for the base test mode in OMS. All other modes cannot benefit from the CA placement accuracy. Such CA placement accuracy is, however, especially critical when defects are located at the edge of a memory device area (such as a static random access memory (SRAM) area) where only use of design-based placement accuracy can guarantee a cell-to-cell based inspection can be performed whereas non-design-based CAs would require a die-to-die based inspection, which is typically lower in sensitivity. In addition, the design cannot be overlaid onto the patch images generated in OMS in the current OMS setup. However, such overlay of the design on the images is very often critical to make sure that the right defect location can be identified. Furthermore, if substantially small CAs (e.g., 7 pixels by 7 pixels) have to be used for nuisance suppression in an inspection, then there is no way in the current OMS setup to guarantee that an area that defines where the defect of interest (DOI) is located (called a "signal box") remains stable at that position for all of the modes selected for use in an OMS process. Slight misplacements of the signal box can lead to different signal-to-noise (S/N) values, which could lead to the wrong best mode.

Accordingly, it would be advantageous to develop systems and methods for selecting one or more modes of an inspection subsystem or system for inspection of a specimen that do not have one or more of the disadvantages described above.

SUMMARY OF THE INVENTION

The following description of various embodiments is not to be construed in any way as limiting the subject matter of the appended claims.

One embodiment relates to a system configured to select one or more modes of an inspection subsystem for inspection of a specimen. The system includes an inspection subsystem that includes at least an energy source, a detector, and a scanning subsystem. The energy source is configured to generate energy that is directed to a specimen by the inspection subsystem. The detector is configured to detect energy from the specimen and to generate output responsive to the detected energy. The scanning subsystem is configured to change a position on the specimen to which the energy is directed and from which the energy is detected.

The system also includes a computer subsystem configured for: a) setting values for one or more parameters of the inspection subsystem to a first mode known to generate output in which patterned features on the specimen are resolved to a degree that allows the output to be aligned to design data for the specimen; b) controlling the scanning subsystem such that the position on the specimen to which the energy is directed and from which the energy is detected is a first position on the specimen at which a first known defect is located; c) acquiring the output generated by the detector at the first position with the first mode; and d) aligning the acquired output to the design data. The computer subsystem is also configured for e) altering the values for the one or more parameters of the inspection subsystem to a second mode different than the first mode; f) without changing the position on the specimen to which the energy is directed and from which the energy is detected from the first position, acquiring the output generated by the detector at the first position with the second mode; and g) repeating steps e) and f) for one or more additional modes of the inspection subsystem.

In addition, the computer subsystem is configured for h) setting the values for the one or more parameters of the inspection subsystem to the first mode; i) controlling the scanning subsystem such that the position on the specimen to which the energy is directed and from which the energy is detected is a second position on the specimen at which a reference for the first position is formed; and j) acquiring the output generated by the detector at the second position with the first mode. The computer subsystem is further configured for k) altering the values for the one or more parameters of the inspection subsystem to the second mode; l) without changing the position on the specimen to which the energy is directed and from which the energy is detected from the second position, acquiring the output generated by the detector at the second position with the second mode; and m) repeating steps k) and l) for the one or more additional modes of the inspection subsystem.

The computer subsystem is also configured for n) repeating steps a) through g) for one or more additional positions on the specimen at which one or more additional known defects are located; repeating steps h) through m) for one or more further positions on the specimen at which one or more references for the one or more additional positions are formed, and p) selecting one or more modes of the inspection subsystem for inspection of the specimen or another specimen of the same type as the specimen based on all of the output generated by all of the steps performed by the computer subsystem. The system may be further configured as described herein.

Another embodiment relates to a method for selecting one or more modes of an inspection system for inspection of a specimen. The method includes steps a) through p) described above. The inspection system is configured as described above with respect to an inspection subsystem. Steps a) through p) are performed by a computer system.

Each of the steps of the method described above may be further performed as described further herein. In addition, the embodiment of the method described above may include any other step(s) of any other method(s) described herein. Furthermore, the method described above may be performed by any of the systems described herein.

Another embodiment relates to a non-transitory computer-readable medium storing program instructions executable on a computer system for performing a computer-implemented method for selecting one or more modes of an inspection system for inspection of a specimen. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design" and "design data" as used herein generally refer to the physical design (layout) of an IC and data derived from the physical design through complex simulation or simple geometric and Boolean operations. In addition, an image of a reticle acquired by a reticle inspection system and/or derivatives thereof can be used as a "proxy" or "proxies" for the design. Such a reticle image or a derivative thereof can serve as a substitute for the design layout in any embodiments described herein that use a design. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In general, however, the design information or data cannot be generated by imaging a wafer with a wafer inspection system. For example, the design patterns formed on the wafer may not accurately represent the design for the wafer and the wafer inspection system may not be capable of generating images of the design patterns formed on the wafer with sufficient resolution such that the images could be used to determine information about the design for the wafer. Therefore, in general, the design information or design data cannot be generated using a physical wafer. In addition, the "design" and "design data" described herein refers to information and data that is generated by semiconductor device designers in a design process and is therefore available for use in the embodiments described herein well in advance of printing of the design on any physical wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

In general, the embodiments described herein are configured for optical mode analysis with design-based care areas. In particular, as described further herein, the embodiments may be used to perform optical mode selection (OMS) with design-based unique care area (CA) placement accuracy and overlay of design (e.g., design file clip) with images (e.g., patch images), or other output of an inspection subsystem or system, while performing OMS. As described further herein, the embodiments enable having design-based accuracy and the design image available for every mode and every defect used for OMS.

In one embodiment, the specimen includes a wafer. In another embodiment, the specimen includes a reticle. The wafer and the reticle may include any wafer and reticle known in the art.

Figure 1:
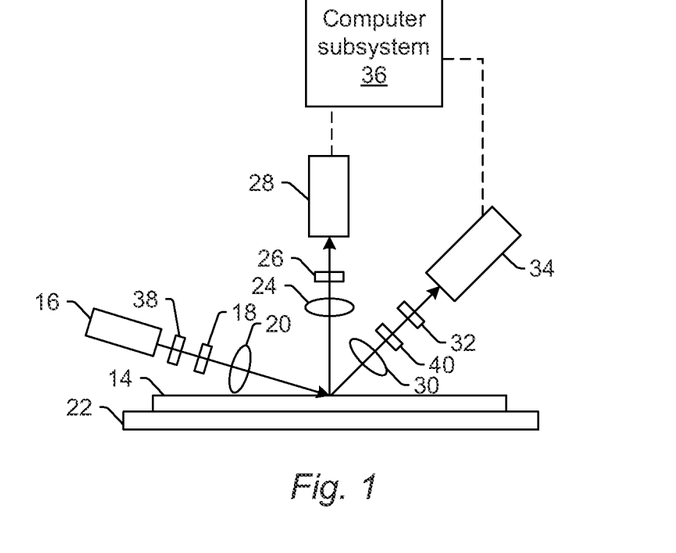
FIGS. 1 and 1a are schematic diagrams illustrating side views of embodiments of a system configured as described herein.

One embodiment relates to a system configured to select one or more modes of an inspection subsystem for inspection of a specimen. One embodiment of such a system is shown in FIG. 1. The inspection subsystem includes at least an energy source, a detector, and a scanning subsystem. The energy source is configured to generate energy that is directed to a specimen by the inspection subsystem. The detector is configured to detect energy from the specimen and to generate output responsive to the detected energy. The scanning subsystem is configured to change a position on the specimen to which the energy is directed and from which the energy is detected.

In one embodiment, the energy directed to the specimen includes light, and the energy detected from the specimen includes light. For example, in the embodiment of the system shown in FIG. 1, the inspection subsystem includes an illumination subsystem configured to direct light to specimen 14. The illumination subsystem includes at least one light source. For example, as shown in FIG. 1, the illumination subsystem includes light source 16. In one embodiment, the illumination subsystem is configured to direct the light to the specimen at one or more angles of incidence, which may include one or more oblique angles and/or one or more normal angles. For example, as shown in FIG. 1, light from light source 16 is directed through optical element 18 and then lens 20 to specimen 14 at an oblique angle of incidence. The oblique angle of incidence may include any suitable oblique angle of incidence, which may vary depending on, for instance, characteristics of the specimen and the defects to be detected on the specimen.

The illumination subsystem may be configured to direct the light to the specimen at different angles of incidence at different times. For example, the system may be configured to alter one or more characteristics of one or more elements of the illumination subsystem such that the light can be directed to the specimen at an angle of incidence that is different than that shown in FIG. 1. In one such example, the system may be configured to move light source 16, optical element 18, and lens 20 such that the light is directed to the specimen at a different oblique angle of incidence or a normal (or near normal) angle of incidence.

In some instances, the inspection subsystem may be configured to direct light to the specimen at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which may be configured differently or the same, or may include at least a light source and possibly one or more other components such as those described further herein. If such light is directed to the specimen at the same time as the other light, one or more characteristics (e.g., wavelength, polarization, etc.) of the light directed to the specimen at different angles of incidence may be different such that light resulting from illumination of the specimen at the different angles of incidence can be discriminated from each other at the detector(s).

In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the specimen. Multiple illumination channels may be configured to direct light to the specimen at the same time or at different times (e.g., when different illumination channels are used to sequentially illuminate the specimen). In another instance, the same illumination channel may be configured to direct light to the specimen with different characteristics at different times. For example in some instances, optical element 18 may be configured as a spectral filter and the properties of the spectral filter can be changed in a variety of different ways (e.g., by swapping out one spectral filter with another) such that different wavelengths of light can be directed to the specimen at different times. The illumination subsystem may have any other suitable configuration known in the art for directing the light having different or the same characteristics to the specimen at different or the same angles of incidence sequentially or simultaneously.

In one embodiment, light source 16 may include a broadband plasma (BBP) light source. In this manner, the light generated by the light source and directed to the specimen may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused onto specimen 14 by lens 20. Although lens 20 is shown in FIG. 1 as a single refractive optical element, it is to be understood that, in practice, lens 20 may include a number of refractive and/or reflective optical elements that in combination focus the light from the optical element to the specimen. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for inspection.

The inspection subsystem also includes a scanning subsystem configured to change the position on the specimen to which the energy is directed and from which the energy is detected and possibly to cause the light to be scanned over the specimen. For example, the inspection subsystem may include stage 22 on which specimen 14 is disposed during inspection. The scanning subsystem may include any suitable mechanical and/or robotic assembly (that includes stage 22) that can be configured to move the specimen such that the light can be directed to and detected from different positions on the specimen. In addition, or alternatively, the inspection subsystem may be configured such that one or more optical elements of the inspection subsystem perform some scanning of the light over the specimen such that the light can be directed to and detected from different positions on the specimen. In instances in which the light is scanned over the specimen, the light may be scanned over the specimen in any suitable fashion such as in a serpentine-like path or in a spiral path.

The inspection subsystem further includes one or more detection channels. At least one of the one or more detection channels includes a detector configured to detect light from the specimen due to illumination of the specimen by the subsystem and to generate output responsive to the detected light. For example, the inspection subsystem shown in FIG.

1 includes two detection channels, one formed by collector 24, element 26, and detector 28 and another formed by collector 30, element 32, and detector 34. As shown in FIG. 1, the two detection channels are configured to collect and detect light at different angles of collection. In some instances, both detection channels are configured to detect scattered light, and the detection channels are configured to detect light that is scattered at different angles from the specimen. However, one or more of the detection channels may be configured to detect another type of light from the specimen (e.g., reflected light).

As further shown in FIG. 1, both detection channels are shown positioned in the plane of the paper and the illumination subsystem is also shown positioned in the plane of the paper. Therefore, in this embodiment, both detection channels are positioned in (e.g., centered in) the plane of incidence. However, one or more of the detection channels may be positioned out of the plane of incidence. For example, the detection channel formed by collector 30, element 32, and detector 34 may be configured to collect and detect light that is scattered out of the plane of incidence. Therefore, such a detection channel may be commonly referred to as a "side" channel, and such a side channel may be centered in a plane that is substantially perpendicular to the plane of incidence.

Although FIG. 1 shows an embodiment of the inspection subsystem that includes two detection channels, the inspection subsystem may include a different number of detection channels (e.g., only one detection channel or two or more detection channels). In one such instance, the detection channel formed by collector 30, element 32, and detector 34 may form one side channel as described above, and the inspection subsystem may include an additional detection channel (not shown) formed as another side channel that is positioned on the opposite side of the plane of incidence. Therefore, the inspection subsystem may include the detection channel that includes collector 24, element 26, and detector 28 and that is centered in the plane of incidence and configured to collect and detect light at scattering angle(s) that are at or close to normal to the specimen surface. This detection channel may therefore be commonly referred to as a "top" channel, and the inspection subsystem may also include two or more side channels configured as described above. As such, the inspection subsystem may include at least three channels (i.e., one top channel and two side channels), and each of the at least three channels has its own collector, each of which is configured to collect light at different scattering angles than each of the other collectors.

As described further above, each of the detection channels included in the inspection subsystem may be configured to detect scattered light. Therefore, the inspection subsystem shown in FIG. 1 may be configured for dark field (DF) inspection of specimens. However, the inspection subsystem may also or alternatively include detection channel(s) that are configured for bright field (BF) inspection of specimens. In other words, the inspection subsystem may include at least one detection channel that is configured to detect light specularly reflected from the specimen. Therefore, the inspection subsystems described herein may be configured for only DF, only BF, or both DF and BF inspection. Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the inspection subsystem may be signals or data, but not image signals or image data. In such instances, a computer subsystem such as computer subsystem 36 of the system may be configured to generate images of the specimen from the non-imaging output of the detectors. However, in other instances, the detectors may be configured as imaging detectors that are configured to generate imaging signals or image data. Therefore, the system may be configured to generate the images described herein in a number of ways.

It is noted that FIG. 1 is provided herein to generally illustrate a configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the 29xx/28xx series of tools that are commercially available from KLA-Tencor, Milpitas, Calif. For some such systems, the methods described herein may be provided as optional functionality of the inspection system (e.g., in addition to other functionality of the inspection system). Alternatively, the inspection subsystem described herein may be designed "from scratch" to provide a completely new inspection system.

Computer subsystem 36 of the system may be coupled to the detectors of the inspection subsystem in any suitable manner (e.g., via one or more transmission media, which may include "wired" and/or "wireless" transmission media) such that the computer subsystem can receive the output generated by the detectors. Computer subsystem 36 may be configured to perform a number of functions using the output of the detectors. For instance, the computer subsystem may be configured to detect defects on the specimen using the output of the detectors. Detecting the defects on the specimen may be performed by the computer subsystem by applying some defect detection algorithm and/or method to the output generated by the detectors. The defect detection algorithm and/or method may include any suitable algorithm and/or method known in the art. For example, the computer subsystem may compare the output of the detectors to a threshold. Any output having values above the threshold may be identified as a potential defect while any output having values below the threshold may not be identified as a potential defect. In another example, the computer subsystem may be configured to send the output of the detectors to a storage medium (not shown in FIG. 1) without performing defect detection on the output. The computer subsystem of the system may be further configured as described herein.

The computer subsystem of the system (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

Although the inspection subsystem is described above as being an optical or light-based inspection system, the inspection subsystem may be an electron beam-based subsystem. In one such embodiment, the energy directed to the specimen includes electrons, and the energy detected from the specimen includes electrons. In one such embodiment shown in FIG. 1a, the inspection subsystem includes electron column 122, and the system includes computer subsystem 124 coupled to the inspection subsystem.

Figure 1A:
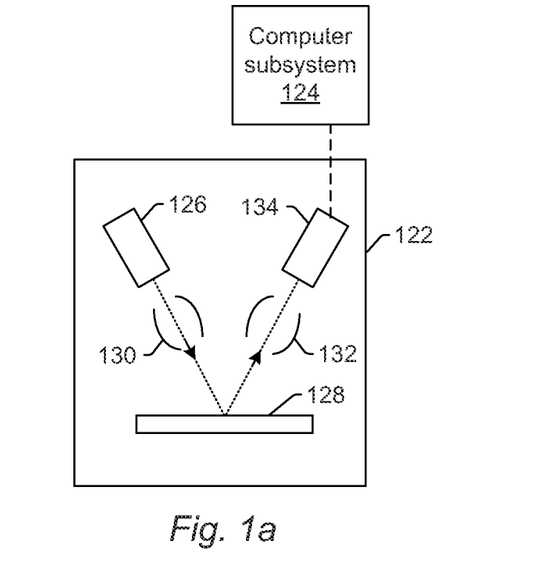

As also shown in FIG. 1a, the electron column includes electron beam source 126 configured to generate electrons that are focused to specimen 128 by one or more elements 130. The electron beam source may include, for example, a cathode source or emitter tip, and one or more elements 130 may include, for example, a gun lens, an anode, a beam limiting aperture, a gate valve, a beam current selection aperture, an objective lens, and a scanning subsystem, all of which may include any such suitable elements known in the art.

Electrons returned from the specimen (e.g., secondary electrons) may be focused by one or more elements 132 to detector 134. One or more elements 132 may include, for example, a scanning subsystem, which may be the same scanning subsystem included in element(s) 130.

The electron column may include any other suitable elements known in the art. In addition, the electron column may be further configured as described in U.S. Pat. No. 8,664,594 issued Apr. 4, 2014 to Jiang et al., U.S. Pat. No. 8,692,204 issued Apr. 8, 2014 to Kojima et al., U.S. Pat. No. 8,698,093 issued Apr. 15, 2014 to Gubbens et al., and U.S. Pat. No. 8,716,662 issued May 6, 2014 to MacDonald et al., which are incorporated by reference as if fully set forth herein.

Although the electron column is shown in FIG. 1a as being configured such that the electrons are directed to the specimen at an oblique angle of incidence and are scattered from the specimen at another oblique angle, it is to be understood that the electron beam may be directed to and scattered from the specimen at any suitable angles. In addition, the electron beam-based inspection subsystem may be configured to use multiple modes to generate output for the specimen as described further herein (e.g., with different illumination angles, collection angles, etc.). The multiple modes of the electron beam-based inspection subsystem may be different in any output generation parameters of the inspection subsystem.

Computer subsystem 124 may be coupled to detector 134 as described above. The detector may detect electrons returned from the surface of the specimen thereby forming electron beam images of (or other output for) the specimen. The electron beam images may include any suitable electron beam images. Computer subsystem 124 may be configured to detect defects on the specimen using output generated by detector 134. Computer subsystem 124 may be configured to perform any additional step(s) described herein. A system that includes the inspection subsystem shown in FIG. 1a may be further configured as described herein.

It is noted that FIG. 1a is provided herein to generally illustrate a configuration of an electron beam-based inspection subsystem that may be included in the embodiments described herein. As with the optical inspection subsystem described above, the electron beam-based inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection system) such as the eSxxx series of tools that are commercially available from KLA-Tencor, Milpitas, Calif. For some such systems, the methods described herein may be provided as optional functionality of the system (e.g., in addition to other functionality of the system). Alternatively, the system described herein may be designed "from scratch" to provide a completely new system.

As further noted above, the inspection subsystem is configured to have multiple modes. In general, a "mode" can be defined by the values of parameters of the inspection subsystem used to generate output of the specimen. Therefore, modes that are different may be different in the values for at least one of the optical or electron beam parameters of the inspection subsystem. For example, in one embodiment in which the energy directed to the specimen and the energy detected from the specimen is light, at least one of the multiple modes uses at least one wavelength of the light directed to the specimen that is different from at least one wavelength of the light directed to the specimen for at least one other of the multiple modes. The modes may be different in the wavelength(s) of light directed to the specimen as described further herein (e.g., by using different light sources, different spectral filters, etc.) for different modes. In another embodiment, at least one of the multiple modes uses an illumination channel of the inspection subsystem that is different from an illumination channel of the inspection subsystem used for at least one other of the multiple modes. For example, as noted above, the inspection subsystem may include more than one illumination channel. As such, different illumination channels may be used for different modes.

In an additional embodiment, at least one of the multiple modes uses a configuration of an aperture of the inspection subsystem that is different from a configuration of an aperture of the inspection subsystem used for at least one other of the multiple modes. The aperture may be an illumination aperture (i.e., an aperture positioned in the path of the energy directed to the specimen) such as aperture 38 shown in FIG. 1 or a collection aperture (i.e., an aperture positioned in the path of the energy collected from the specimen) such as aperture 40 shown in FIG. 1. For example, if energy is directed to the specimen in different paths for different modes, then different apertures having at least one different characteristic (e.g., shape or size) may be positioned in the different paths. In another example, if energy is directed to the specimen in the same path for different modes, then different apertures having at least one different characteristic may be positioned in the path at different times to sequentially generate images for the specimen. In similar manners, the aperture in the path of energy from the specimen may be different for different modes by having different apertures having at least one different characteristic in the path of different energy from the specimen or by switching the aperture in the path of the energy between different scans with different modes.

As described above, therefore, the different modes may be different in illumination and/or collection/detection. The different modes may also or alternatively have other differences in collection/detection. For example, in one embodiment, at least one of the multiple modes uses a detector of the inspection subsystem that is different from a detector of the inspection subsystem used for at least one other of the multiple modes. In some such embodiments, as described further above, the inspection subsystem may include multiple detectors. Therefore, one of the detectors may be used for one mode and another of the detectors may be used for another mode. Furthermore, the modes may be different from each other in more than one way described herein (e.g., different modes may have one or more different illumination parameters and one or more different detection parameters).

The computer subsystem is configured for a) setting values for one or more parameters of the inspection subsystem to a first mode known to generate output in which patterned features on the specimen are resolved to a degree that allows the output to be aligned to design data for the specimen. For example, a test that is valid for design-based CAs can be used as the base test (also called "mode 1" herein) for the OMS analysis described herein. Therefore, the first mode (or mode 1) can be used as the base test mode. The first mode may be determined (and therefore known) to generate output in which patterned features are resolved to a degree that allows the output to be aligned to design data for the specimen empirically or experimentally. For example, a mode may be selected that is expected to produce output suitable for alignment to the design data, output may be acquired by the inspection subsystem using the mode, and then alignment of the output to the design data may be attempted. If the output can be successfully aligned to the design data (which may be determined in any suitable manner such as displaying results of the alignment attempt to a user and prompting the user for information about the success of the alignment attempt), then that mode may be selected as the first mode.

The patterned features for which output is aligned to the design data may include the patterned features at the location of a defect (or a reference for the defect). In other words, the patterned features for which output is aligned to design data include patterned features that will form actual device features in the device and do not include patterned features that are simply alignment marks included in the design data, which have no functionality in the device being formed on the specimen, and/or other alignment points on the specimen (e.g., a corner of a die on the specimen). In particular, as described further herein, the alignment of the output generated by the first mode to design data is performed using the patterned features and the design data at the location of the defect. Therefore, the patterned features for which output is aligned to the design data will be patterned features having dimensions equal to (or not much larger than) the critical dimension (i.e., the smallest dimension) of the device being formed on the specimen.

The design-based CAs described herein are "design-based" in that their locations in the output are not determined based on a reference point in the output that corresponds to some reference point on the specimen (e.g., an alignment mark or a die corner). Instead, the design-based CAs are "design-based" in that their locations are determined based on alignment of the output generated for the specimen with design data for the specimen, which may be performed as described herein based on the patterned features in the output and the design. The design-based CAs can also have substantially smaller dimensions than other non-design-based CAs. For example, since the design-based CAs are identified in the output based on the patterned features themselves, the design-based CAs can have a size that is on the order of a few patterned features (since normally the design-based CAs would need more than just one patterned feature to provide accurate alignment of the output to the design data). As such, the design-based CAs can have a size in the output that is on the order of only a few pixels. For example, the design-based CAs can have a size of 10 or fewer pixels by 10 or fewer pixels. In this manner, the design-based CAs described herein may also be referred to as micro care areas (or MCAs). In particular, the design-based CAs may be considered MCAs because of their substantially small size (e.g., having dimensions that are less than 1 um). Such substantially small CAs are enabled at least in part due to the fact that the CA locations are determined by aligning the output generated by the inspection subsystem to the design data. For example, such alignment that can be performed as described further herein can enable the design data space positions of the output generated by the inspection subsystem to be determined with sub-pixel accuracy. Therefore, the CA sizes may be reduced accordingly because the position of the CAs can be determined in the output with similar accuracy.

Setting the values for the one or more parameters to the first mode may be performed in any suitable manner, and the one or more parameters of the first mode may include any of the parameters described herein. For example, setting the one or more values for the one or more parameters to the first mode may include setting one or more values for one or more parameters for directing energy to the specimen and/or for detection of energy from the specimen. In one such example, for a light-based inspection subsystem, the parameter(s) may include parameter(s) of a light source, a spectral filter, a polarizing filter, an apodizer, an aperture, a detector, etc. The values of such parameter(s) may include, for example, the wavelength(s), polarization(s), angle(s) of incidence, etc. of light directed to the specimen and the wavelength(s), polarization(s), angle(s) of collection, etc. of light detected from the specimen. The computer subsystem may be configured to set the parameter(s) by directly controlling one or more elements of the inspection subsystem or indirectly by sending instructions for setting the parameters to one or more controllers or control subsystems (not shown) of the inspection subsystem.

The computer subsystem is also configured for b) controlling the scanning subsystem such that the position on the specimen to which the energy is directed and from which the energy is detected is a first position on the specimen at which a first known defect is located. For example, the computer subsystem may move the stage described further herein to the position of the first known defect (or defect 1). However, the computer subsystem may control any other component(s) of the inspection subsystem (e.g., one or more optical elements that are capable of performing some scanning of the energy over the specimen) such that the position on the specimen to which the energy is directed and from which the energy is detected is the first position.

The position on the specimen to which the energy is directed and from which the energy is detected may also be referred to as the field of view (FOV) of the inspection subsystem on the specimen. In this case, the first position may be located at the center of the FOV to maximize the possibility that the actual location of the first known defect is somewhere within the area of the FOV of the inspection subsystem on the specimen.

The first known defect may be known in any suitable manner. For example, one or more test inspections may be performed on the specimen to identify defects of interest (DOIs) and nuisance defects thereon. The results of the one or more test inspections may be verified by defect review to ensure that the DOIs identified by inspection are actually DOIs and the nuisance defects identified by inspection are actually nuisance defects. The first known defect may be a DOI. In this instance, the one or more modes may be selected as described further herein to ensure that the selected mode(s) can detect the DOI. However, the first known defect may be a nuisance defect. In this manner, the one or more modes may be selected as described further herein to ensure that the selected mode(s) do not detect the nuisance defect.

The computer subsystem is further configured for c) acquiring the output generated by the detector at the first position with the first mode. The output may be acquired at the first position with the first mode in any suitable manner. For example, once the first position is centered in the FOV of the inspection subsystem and the parameters of the inspection subsystem are set to the first mode, output generated by one or more detectors of the inspection subsystem may be acquired by the computer subsystem. In essence therefore, the computer subsystem may perform an image grab at the first position using the first mode. Although some embodiments of the methods are described herein with respect to "images," the output used in any of the embodiments described herein may be any of the output described herein (e.g., images, image data, image signals, non-image data, non-image signals, etc.).

In this manner, acquiring the output generated by the detector at the first position with the first mode may include acquiring the output at a discrete location on the specimen. As such, acquiring this output may not include scanning the energy over a relatively large portion of the specimen while the energy is being detected from the specimen as would be performed in a regular inspection process performed on a specimen. In addition, acquiring the output at the first position with the first mode may include scanning the energy over the discrete location of the first position while detecting energy from the specimen. However, positioning the first position within the FOV of the inspection subsystem and then acquiring the output of the detector without scanning the energy over the specimen (such that the position of the FOV is stationary on the specimen during the output acquisition) may be more appropriate for the embodiments described herein.

The computer subsystem is also configured for d) aligning the acquired output to the design data. In this manner, the computer subsystem may perform design-based alignment of the output acquired at the first position of the first known defect in the first mode to the design data. Design-based alignment of the acquired output to the design data may be performed in any suitable manner (e.g., by pattern matching). The design data that is aligned to the acquired output may include any of the design data described herein.

Performing design-based alignment of the acquired output to design data may be further performed as described in U.S. Pat. No. 7,676,077 to Kulkarni et al. issued on Mar. 9, 2010, U.S. Pat. No. 8,041,103 to Kulkarni et al. issued on Oct. 18, 2011, and U.S. Pat. No. 8,139,843 to Kulkarni et al. issued on Dec. 17, 2013, which are incorporated by reference as if fully set forth herein. The embodiments described herein may be further configured to perform any step(s) described in these patents and may be further configured as described in these patents.

The computer subsystem may also be configured for determining an area of a signal box in the acquired output based on results of aligning the acquired output to the design data. For example, once the design data has been aligned to the acquired output, a comparison between the design data (or another suitable reference) and the acquired output aligned thereto may be performed. Any differences between the design data (or reference) and the acquired output (or any differences above a predetermined threshold) may be identified as being part of the defect. For example, if the acquired output is an image, then any pixels in the acquired output that are different enough from the design (or reference) may be identified as defective pixels. In addition, any other type of defect detection may be performed on the output acquired at the first position to thereby determine the area of the defect and therefore the signal box in the output acquired at the first position. Those defective pixels may then be designated as being part of the signal box for the defect. For example, the area of the signal box may be determined to be the same as the area surrounding all of the defective pixels. In this manner, a "signal box" may or may not have a box-like shape (e.g., it may be polygonal or free form). Alternatively, the signal box may be determined as a box that surrounds all of the defective pixels (and may therefore include some non-defective pixels in instances in which a defect is not rectangular). Since the signal box for the first known defect can be determined based on alignment of the output for the first known defect generated with the first mode to design data, the embodiments described herein provide improved signal box placement accuracy.

In one embodiment, aligning the acquired output to the design data includes overlaying a portion of the design data with the acquired output or an image generated from the acquired output. For example, the design data may be overlaid on the acquired output in multiple positions within the acquired output until a match between the design data and the acquired output is found at one of the overlay positions. In this manner, the aligning may include "sliding the design data around" within the acquired output until alignment can be achieved. Once the alignment has been performed, the overlay of the design data with the acquired output can be used for additional steps described herein. Therefore, the embodiments described herein enable design overlay in OMS. The portion of the design that is overlaid with the output may include, for example, a design clip or a relatively small portion of the entire design data that may include only a few (e.g., less than 10) patterned features. For example, the portion of the design data that is overlaid with the output may include only the design data for a single CA having a substantially small size as described further herein.

In another embodiment, aligning the acquired output to the design data includes overlaying the design data on the output acquired at the first position with the first mode, and the computer subsystem is configured for displaying results of the overlaying to a user and prompting the user to select an area of the first known defect in the acquired output based on the displayed results. For example, the computer subsystem may acquire the output (e.g., collect the candidate image) of the first known defect for mode 1 and show the design clip overlay with the acquired output so that a user can easily adjust the signal and noise boxes. The signal box can be defined by the user selecting or identifying the portions of the acquired output that correspond to the defect. A "noise box" may be an area of the acquired output that does not correspond to the defect (and therefore corresponds to noise in the output). Therefore, a noise box may be identified by the user by selecting or identifying one or more portions of the acquired output that do not correspond to the defect.

The computer subsystem is configured for e) altering the values for the one or more parameters of the inspection subsystem to a second mode different than the first mode. The computer subsystem may alter the values for the one or more parameters of the inspection subsystem from the first mode to the second mode in any suitable manner. For example, the computer subsystem may alter one or more parameters of a spectral filter of the inspection subsystem such that the wavelength(s) of light that is/are directed to the specimen can be different. The first and second modes may, however, be different in any one or more parameters described herein. The second mode may or may not be a mode that is known to generate output in which patterned features on the specimen are resolved to a degree that allows the output to be aligned to design data for the specimen. For example, as described further herein, results of the alignment of the output generated using the first mode to the design data may be used to align the output generated with all other modes to the design data without requiring actually performing alignment between the output generated using modes other than the first mode and the design data. In this manner, the second mode, and all other modes described herein, may have unknown capability for resolving patterned features formed on the specimen.

The computer subsystem is further configured for f) without changing the position on the specimen to which the energy is directed and from which the energy is detected from the first position, acquiring the output generated by the detector at the first position with the second mode. For example, the computer subsystem may keep the stage position unchanged and collect the candidate image or other output for defect 1 for mode 2. In other words, the computer subsystem does not change the position of the FOV of the inspection subsystem on the specimen between acquisition of the output with the first mode and the second mode. Acquiring the output generated by the detector at the first position with the second mode may otherwise be performed as described further herein.

Figure 2:
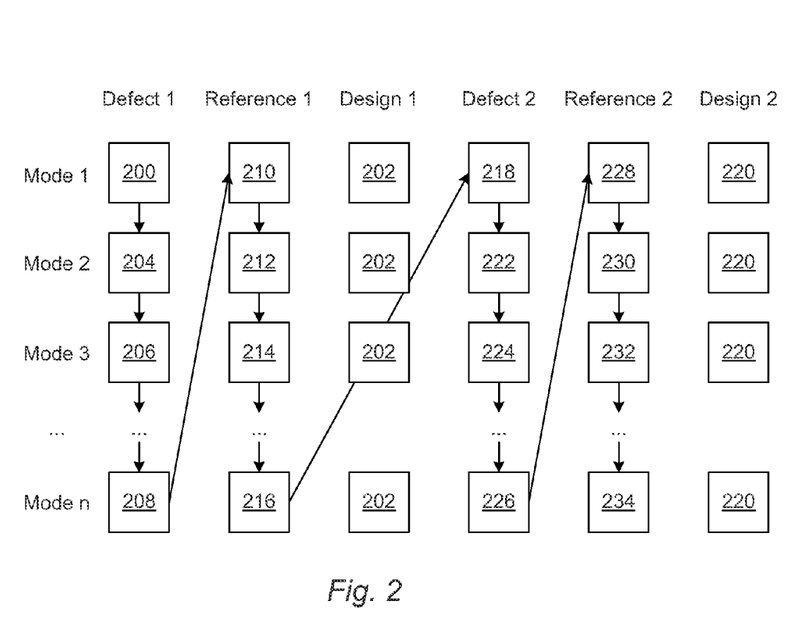
FIG. 2 is a schematic diagram illustrating one embodiment of a flow chart for performing steps described herein.

The computer subsystem is also configured for g) repeating steps e) and f) for one or more additional modes of the inspection subsystem. For example, the computer subsystem may continue to collect candidate images or other output for defect 1 for all remaining modes. In this manner, the computer subsystem may be configured to acquire a number of different output or images at the location of the defect by changing the mode of the inspection subsystem after each output or image has been acquired but without altering a position of the FOV of the inspection subsystem on the specimen. For example, FIG. 2 shows a sequence for collecting image data for defects and references for each mode. In particular, as shown in FIG. 2, for defect 1, image 200 may be acquired with mode 1 of the inspection subsystem as described further herein. This image is then aligned to design 202 for the defect location, which may be performed as described further herein. Results of the alignment of the output to the design may be used to determine the defect location in the output with substantially high accuracy. After design-based alignment is performed for defect 1 and mode 1, output for all optical modes may be collected for defect 1. In particular, without changing the position on the specimen to which energy is directed and from which energy is detected from that used for mode 1, image 204 may be acquired with mode 2, image 206 may be acquired with mode 3, and so on, until image 208 is acquired with mode n. Images of design 202 may also be shown for all defects.

The one or more additional modes of the inspection subsystem for which steps e) and f) are repeated may include all of the available or possible modes of the inspection subsystem. For example, the embodiments described herein may be used to analyze every different combination of values of parameters of the inspection subsystem in a relatively timely manner. However, the embodiments described herein may also be used to analyze only a portion of all of the available or possible modes of the inspection subsystem, which may be selected in any suitable manner.

In one embodiment, the computer subsystem is further configured for determining an area of the first known defect in the acquired output generated by the detector at the first position with the first mode, the second mode, and the one or more additional modes based on results of aligning the acquired output to the design data. For example, as described above, the area of the first known defect in the output acquired with the first mode can be determined based on results of aligning the acquired output generated with the first mode to the design data. Then, since the position on the specimen to which energy is directed and from which energy is detected is not changed after the output is acquired at the first position with the first mode, the within-output position of the first known defect determined using the first mode will be the same in the acquired output generated with all of the other modes. Of course, if different modes have some change in the FOV or the configuration (e.g., area, pixel size, magnification, etc.) of the collection or detection, the within-output position of the area of the first known defect may change somewhat within the acquired output generated with different modes. However, based on knowledge of how the different modes are different and the area of the first known defect in the acquired output generated with the first mode, the area of the first known defect in the acquired output generated with other modes can be determined substantially accurately.

In another embodiment, the computer subsystem is further configured for overlaying the design data with the acquired output generated by the detector at the first position with the second mode and the one or more additional modes based on results of aligning the acquired output to the design data. For example, the design data can be overlaid to the defect for all modes based on the results of aligning the design data to the output generated using the first mode, thereby allowing identification of the defect location in the output generated using all modes with substantially high confidence. For example, as shown in FIG. 2, based on information about where the defect is located in image 200, design 202 may be overlaid on images 204, 206, and 208 based on the known spatial relationship of the output acquired with different modes and the known spatial relationship between the output acquired with the first mode and the design data. In this manner, information about the defect image in images 204, 206, and 208 relative to the design may be determined.

An alternative to the embodiments described herein would be to try to perform alignment between design and output for every mode being considered in OMS. However, such an alternative would be substantially risky in that the alignment may not be successful or possible for many modes such as those in which the patterned features on the specimen are not resolved in the output with sufficient resolution such that the patterned features in the output can be aligned to the patterned features in the design. In addition, such an alternative would be substantially time consuming (e.g., since the alignment of design to output for modes in which the patterned features are not resolved with sufficient accuracy to allow easy alignment of patterned features in the design to patterned features in the output will take a much longer time than situations in which the patterned features are resolved with substantially good resolution).

Therefore, one advantage of the embodiments described herein is that the design-based placement accuracy of CAs can be used for all modes and not just for the base test mode. This placement accuracy is achieved by collecting all the candidate/reference images for one defect through all modes before going to the next defect and keeping the FOV on the specimen at the same position during output acquisition with all modes. In contrast, the current OMS setup methods move the stage from defect-to-defect until all the data is collected for mode 1 and afterwards the same is done for mode 2.

In a further embodiment, the computer subsystem is configured for determining an area of the first known defect in the acquired output generated by the detector at the first position with the second mode and the one or more additional modes without aligning the acquired output generated by the detector at the first position with the second mode and the one or more additional modes to the design data. For example, the embodiments described herein provide improved signal box placement accuracy within all output generated with all modes, not just the modes that generate output suitable for alignment of the output to design. In other words, without aligning design data to the output acquired with modes other than the first mode, the spatial relationship between the output generated in different modes (enabled by the stationary FOV on the specimen during output acquisition with all modes) and the spatial relationship between the design and the output generated using the first mode (provided by the design-to-output alignment performed for the output generated with the first mode) can be used in combination to determine the design-based positions of the output acquired in all other modes.

In addition, the computer subsystem is configured for h) setting the values for the one or more parameters of the inspection subsystem to the first mode. For example, the computer subsystem may dial in mode 1 (or the base test mode). This step may be performed as described further herein (e.g., with respect to step a)).

The computer subsystem is further configured for i) controlling the scanning subsystem such that the position on the specimen to which the energy is directed and from which the energy is detected is a second position on the specimen at which a reference for the first position is formed. For example, the computer subsystem may move the stage to a first reference (or reference 1) of defect 1. Controlling the scanning subsystem in this step may be performed as described further herein.

In one embodiment, the first position is located within a first design-based CA, and patterned features in the reference for the first position are the same as patterned features within the first design-based CA. For example, the reference for the first position may vary depending on the type of inspection that will be performed for the specimen. In one embodiment, the first known defect and the reference for the first position are located in different cells in a memory area of a device being formed on the specimen. For example, if the inspection is a cell-to-cell inspection, then the reference may be located at a second position that is within the same die as the first position. In particular, the first and second positions may be located at different cells in the same die on the specimen. In contrast, if the inspection is a die-to-die type inspection, then the reference may be located at a second position that is within a different die than the first position. In this manner, the first and second positions may be located in different dies on the specimen and the same within-die position in the different dies. Of course, any other reference is suitable for use in the embodiments described herein as long as first position of the first known defect and the second position of the reference are positions of the same patterned features in the design. Therefore, the second position on the specimen that is positioned in the FOV of the inspection subsystem may be determined based on the first position and information about the patterned features in the design (e.g., cell pitch, die pitch, etc.).

The computer subsystem is also configured for j) acquiring the output generated by the detector at the second position with the first mode. For example, the computer subsystem may collect the reference 1 image for defect 1 for mode 1. Acquiring the output generated at the second position may be performed as described further herein with respect to acquiring the output generated at the first position.

In one embodiment, the computer subsystem is further configured for aligning the acquired output generated by the detector at the second position with the first mode to the design data for the specimen. For example, the computer subsystem may move the FOV of the inspection subsystem to a first reference (or reference 1) of defect 1 and perform design-based alignment. Such aligning may be further performed as described herein.

In another embodiment, the computer subsystem is configured for determining an area of the reference for the first position in the acquired output generated by the detector at the second position with the first mode by aligning the acquired output generated by the detector at the second position with the first mode to the design data. Determining the area of the reference may be performed as described further herein.

The computer subsystem is further configured for k) altering the values for the one or more parameters of the inspection subsystem to the second mode. Altering the values for the one or more parameters of the inspection subsystem to the second mode may be performed as described further herein.

In addition, the computer subsystem is configured for l) without changing the position on the specimen to which the energy is directed and from which the energy is detected from the second position, acquiring the output generated by the detector at the second position with the second mode. For example, the computer subsystem may be configured for keeping the FOV position on the specimen unchanged and collecting the reference 1 image of defect 1 for mode 2. Acquiring the output in this step may be further performed as described herein.

The computer subsystem is also configured for m) repeating steps k) and l) for the one or more additional modes of the inspection subsystem. The one or more additional modes for which step m) is performed may include all of the one or more additional modes for which step g) is performed. For example, the computer subsystem may be configured for acquiring reference 1 images (or other output) for defect 1 for all modes. In one such example, as shown in FIG. 2, the computer subsystem may be configured to acquire image 210 for reference 1 for defect 1 with mode 1. After design-based alignment is performed for reference 1 with mode 1 output, output for all optical modes may be collected at the position of reference 1. For example, after image 210 has been aligned to design to determine the position of the reference in the output with substantially high accuracy, image 212 for reference 1 may be acquired with mode 2, image 214 for reference 1 may be acquired with mode 3, and so on, until image 216 is acquired for reference 1 with mode n.

In some embodiments, the computer subsystem is configured for performing steps h) through m) for another position on the specimen at which another reference for the first position is formed. For example, the computer subsystem may be configured for performing steps h) through m) for all required reference images or other output of defect 1. The other reference may include any of the references described herein. For example, the reference and the other reference may be located at two different cells in the same die as the first known position. In another example, the reference and the other reference may be located in two different dies at the same within-die position as the first known position in another die on the specimen. In this manner, output may be generated for all of the first and second modes and the one or more additional modes for multiple references for a first known defect position, which may be particularly useful for instances in which the inspection to be performed on the specimen includes double arbitration type defect detection in which a test image is compared to two different references in order to identify which of the images includes the difference and therefore the defect.

The computer subsystem is further configured for n) repeating steps a) through g) for one or more additional positions on the specimen at which one or more additional known defects are located. For example, the computer subsystem may be configured for performing steps a) through g) for all defects (and/or nuisances) that have been selected and marked for OMS. The one or more additional known defects may otherwise be selected as described herein.

In one such example, as shown in FIG. 2, image 218 for defect 2 may be acquired with mode 1. After design-based alignment is performed for defect 2 using the image generated with mode 1, output for all optical modes may be acquired at the position of defect 2. In particular, portion of design 2 corresponding to the location of defect 2 may be aligned to image 218 for defect 2 to thereby determine the position of defect 2 in image 218 with substantially high accuracy. Then, without changing the position on the specimen to which the energy is directed and from which the energy is detected, image 222 may be acquired with mode 2, image 224 may be acquired with mode 3, and so on, until image 226 is acquired with mode n. Design images may also be shown for all images acquired for defect 2.

In one embodiment, the first position is located within a first design-based CA, and the one or more additional positions are located within other design-based CAs different than the first. For example, each of the defects for which output is generated as described herein may be located within a different design-based CA. Therefore, the embodiments described herein may be used to generate output suitable for OMS for different design-based CAs.

In another embodiment, at least one of the first known defect and the one or more additional known defects is located at an edge of a memory area of a device being formed on the specimen. For example, defects that fall outside of non-design-based CAs but are inside of design-based CAs may be evaluated by cell-to-cell comparisons or inspection if the CA is, for example, a static random access memory (SRAM) device CA. In other words, the embodiments described herein enable performing cell-to-cell comparisons in OMS even when a defect is too close to the SRAM edge to be included in a non-design-based CA and falls in a CA border area of currently used, non-design-based CAs.

In addition, the computer subsystem is configured for o) repeating steps h) through m) for one or more further positions on the specimen at which one or more references for the one or more additional positions are formed. For example, the computer subsystem may be configured for acquiring reference 2 images or other output for defect 2 for all modes. For example, as shown in FIG. 2, the computer subsystem may be configured to acquire image 228 for reference 2 for defect 2 with mode 1. After design-based alignment is performed for reference 2 with mode 1 output, output for all optical modes may be collected at the position of reference 2. For example, after image 228 has been aligned to design 220 to determine the position of the reference in the output with substantially high accuracy, image 230 for reference 2 may be acquired with mode 2, image 232 for reference 2 may be acquired with mode 3, and so on, until image 234 is acquired for reference 2 with mode n.

The computer subsystem is also configured for p) selecting one or more modes of the inspection subsystem for inspection of the specimen or another specimen of the same type as the specimen based on all of the output generated by all of the steps performed by the computer subsystem. Selecting the mode(s) for the inspection of the specimen may be performed in any suitable manner known in the art. In other words, once the output described herein has been generated, it is suitable for use in any method or system for selecting a mode or modes for inspection of a specimen. In one such example, the output for one mode and one defect may be compared to the output for one or more references of the defect acquired in the same, one mode. Based on results of the comparison, difference images may be generated. In addition, based on results of the comparison, one or more characteristics of the defect in the output or the difference images can be determined such as a signal or a signal-to-noise ratio of the defect for the one mode. Such steps may be performed for one or more other modes. The mode or modes that generate the best signal or signal-to-noise ratio for a defect may then be selected for use in inspection of the specimen or another specimen of the same type. Similar steps may be performed when the output is generated for a location of a nuisance on the wafer except that the mode or modes that generate the lowest signal or signal-to-noise ratio for the location of the nuisance may be selected for use in the inspection. Any other measure(s) of detectability of DOIs and/or suppression of nuisances (e.g., DOI capture rate, nuisance rate, etc.) in the comparisons of the output generated at the location of known DOIs and/or known nuisances with different modes may be used to select one or more of the modes being considered for use in the inspection.

In an additional embodiment, the inspection is a cell-to-cell inspection performed in a memory area of a device being formed on the specimen. The cell-to-cell inspection may include any cell-to-cell inspection described herein or known in the art. In addition, the memory area of the device may include any memory area described herein or known in the art of any device described herein or known in the art. In addition, although the embodiments described herein may be particularly advantageous for OMS for cell-to-cell inspection, the embodiments described herein may be used for any type of inspection (e.g., die-to-die inspection, die-to-standard reference die inspection, etc.) known in the art.

In another embodiment, the first known defect and the reference for the first position are located in different cells in a memory area of a device being formed on the specimen, and selecting the one or more modes includes performing cell-to-cell comparisons of the output acquired at the first position and the second position with the same modes. For example, as described further herein, the first known defect and its reference(s) may be located at different positions of different cells in the same die on the specimen. Therefore, comparisons of the output at the defect position and the reference position performed to assess detectability of the defect (or suppression of the nuisance) may include cell-to-cell comparisons of the output generated using the same mode. Selecting the mode(s) for use in the inspection may otherwise be performed as described herein.

In this manner, the embodiments described herein can be used to help find the best optical or electron beam conditions to detect a defect. With the previously used methods for performing OMS, this might be, in some cases, impossible or substantially time consuming. However, the embodiments described herein can be used to select the mode(s) to be used for inspection relatively quickly and easily. In addition, the embodiments described herein can be used to select inspection mode(s) for inspection to be performed for detecting new defect types on a specimen. Therefore, the embodiments described herein can be used for closing gaps in the defect detection ability of an inspection when a new defect arises. Closing defect gaps within a relatively short amount of time is crucial for chip manufacturers and can save them millions of dollars.

Each of the embodiments of the system described above may be combined together into one single embodiment. In other words, unless otherwise noted herein, none of the system embodiments are mutually exclusive of any other system embodiments.

Another embodiment relates to a method for selecting one or more modes of an inspection system for inspection of a specimen. The method includes steps a) through p) described above. The inspection system is configured as described herein with respect to an inspection subsystem. Steps a) through p) are performed by a computer system, which may be configured as described herein.

Each of the steps of the method may be performed as described further herein. The method may also include any other step(s) that can be performed by the inspection subsystem and/or computer subsystem(s) described herein. In addition, the method described above may be performed by any of the system embodiments described herein.

Figure 3:
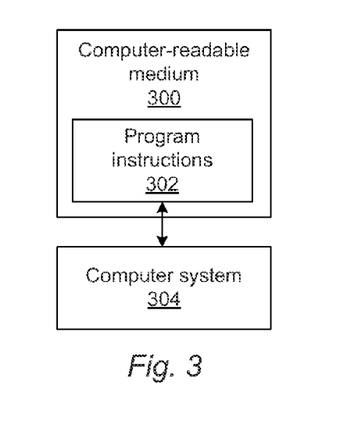
FIG. 3 is a block diagram illustrating one embodiment of a non-transitory computer-readable medium storing program instructions for causing a computer system to perform a computer-implemented method described herein.

An additional embodiment relates to a non-transitory computer-readable medium storing program instructions executable on a computer system for performing a computer-implemented method for selecting one or more modes of an inspection system for inspection of a specimen. One such embodiment is shown in FIG. 3. In particular, as shown in FIG. 3, non-transitory computer-readable medium 300 includes program instructions 302 executable on computer system 304. The computer-implemented method may include any step(s) of any method(s) described herein.

Program instructions 302 implementing methods such as those described herein may be stored on computer-readable medium 300. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 304 may be configured according to any of the embodiments described herein.

Further modifications and alternative embodiments of various aspects of the invention will be apparent to those skilled in the art in view of this description. For example, methods and systems for selecting one or more modes of an inspection subsystem or system for inspection of a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to select one or more modes of an inspection subsystem for inspection of a specimen, comprising:

an inspection subsystem comprising at least an energy source, a detector, and a scanning subsystem, wherein the energy source is configured to generate energy that is directed to a specimen by the inspection subsystem, wherein the detector is configured to detect energy from the specimen and to generate output responsive to the detected energy, wherein the scanning subsystem is configured to change a position on the specimen to which the energy is directed and from which the energy is detected, and wherein the scanning subsystem comprises a mechanical assembly configured to move the specimen and a stage on which the specimen is disposed; and a computer subsystem, wherein the computer subsystem is a device having one or more processors executing instructions from a memory medium, and wherein the computer subsystem is configured for:

a) setting values for one or more parameters of the inspection subsystem to a first mode known to generate output in which patterned features on the specimen are resolved to a degree that allows the output to be aligned to design data for the specimen;

b) controlling the scanning subsystem such that the position on the specimen to which the energy is directed and from which the energy is detected is a first position on the specimen at which a first known defect is located;

c) acquiring the output generated by the detector at the first position with the first mode;

d) aligning the acquired output to the design data;

e) altering the values for the one or more parameters of the inspection subsystem to a second mode different than the first mode;

f) without changing the position on the specimen to which the energy is directed and from which the energy is detected from the first position, acquiring the output generated by the detector at the first position with the second mode;

g) repeating steps e) and f) for one or more additional modes of the inspection subsystem;

h) setting the values for the one or more parameters of the inspection subsystem to the first mode;

i) controlling the scanning subsystem such that the position on the specimen to which the energy is directed and from which the energy is detected is a second position on the specimen at which a reference for the first position is formed;

j) acquiring the output generated by the detector at the second position with the first mode;

k) altering the values for the one or more parameters of the inspection subsystem to the second mode;

l) without changing the position on the specimen to which the energy is directed and from which the energy is detected from the second position, acquiring the output generated by the detector at the second position with the second mode;

m) repeating steps k) and l) for the one or more additional modes of the inspection subsystem;

n) repeating steps a) through g) for one or more additional positions on the specimen at which one or more additional known defects are located;

o) repeating steps h) through m) for one or more further positions on the specimen at which one or more references for the one or more additional positions are formed; and p) selecting one or more modes of the inspection subsystem for inspection of the specimen or another specimen of the same type as the specimen based on all of the output generated by all of the steps performed by the computer subsystem.

2. The system of claim 1, wherein the first position is located within a first design-based care area, and wherein the one or more additional positions are located within other design-based care areas different than the first.

3. The system of claim 1, wherein aligning the acquired output to the design data comprises overlaying a portion of the design data with the acquired output or an image generated from the acquired output.

4. The system of claim 1, wherein at least one of the first known defect and the one or more additional known defects is located at an edge of a memory area of a device being formed on the specimen.

5. The system of claim 1, wherein the first known defect and the reference for the first position are located in different cells in a memory area of a device being formed on the specimen.

6. The system of claim 1, wherein the first known defect and the reference for the first position are located in different cells in a memory area of a device being formed on the specimen, and wherein selecting the one or more modes comprises performing cell-to-cell comparisons of the output acquired at the first position and the second position with the same modes.

7. The system of claim 1, wherein the inspection is a cell-to-cell inspection performed in a memory area of a device being formed on the specimen.

8. The system of claim 1, wherein the computer subsystem is further configured for aligning the acquired output generated by the detector at the second position with the first mode to the design data for the specimen.

9. The system of claim 1, wherein the first position is located within a first design-based care area, and wherein patterned features in the reference for the first position are the same as patterned features within the first design-based care area.

10. The system of claim 1, wherein the computer subsystem is further configured for determining an area of the first known defect in the acquired output generated by the detector at the first position with the first mode, the second mode, and the one or more additional modes based on results of said aligning the acquired output to the design data.

11. The system of claim 1, wherein the computer subsystem is further configured for overlaying the design data with the acquired output generated by the detector at the first position with the second mode and the one or more additional modes based on results of said aligning the acquired output to the design data.

12. The system of claim 1, wherein the computer subsystem is further configured for determining an area of the first known defect in the acquired output generated by the detector at the first position with the second mode and the one or more additional modes without aligning the acquired output generated by the detector at the first position with the second mode and the one or more additional modes to the design data.

13. The system of claim 1, wherein aligning the acquired output to the design data comprising overlaying the design data on the output acquired at the first position with the first mode, and wherein the computer subsystem is further configured for displaying results of said overlaying to a user and prompting the user to select an area of the first known defect in the acquired output based on the displayed results.

14. The system of claim 1, wherein the computer subsystem is further configured for determining an area of the reference for the first position in the acquired output generated by the detector at the second position with the first mode by aligning the acquired output generated by the detector at the second position with the first mode to the design data.

15. The system of claim 1, wherein the computer subsystem is further configured for performing steps h) through m) for another position on the specimen at which another reference for the first position is formed.

16. The system of claim 1, wherein the specimen comprises a wafer.

17. The system of claim 1, wherein the energy directed to the specimen comprises light, and wherein the energy detected from the specimen comprises light.

18. The system of claim 1, wherein the energy directed to the specimen comprises electrons, and wherein the energy detected from the specimen comprises electrons.

19. A non-transitory computer-readable medium, storing program instructions executable on a computer system for performing a computer-implemented method for selecting one or more modes of an inspection system for inspection of a specimen, wherein the computer system is a device having one or more processors executing the program instructions from the non-transitory computer-readable medium, and wherein the computer-implemented method comprises:

a) setting values for one or more parameters of the inspection system to a first mode known to generate output in which patterned features on the specimen are resolved to a degree that allows the output to be aligned to design data for the specimen, wherein the inspection system comprises at least an energy source, a detector, and a scanning subsystem, wherein the energy source is configured to generate energy that is directed to a specimen by the inspection system, wherein the detector is configured to detect energy from the specimen and to generate output responsive to the detected energy, wherein the scanning subsystem is configured to change a position on the specimen to which the energy is directed and from which the energy is detected, and wherein the scanning subsystem comprises a mechanical assembly configured to move the specimen and a stage on which the specimen is disposed;

b) controlling the scanning subsystem such that the position on the specimen to which the energy is directed and from which the energy is detected is a first position on the specimen at which a first known defect is located;

c) acquiring the output generated by the detector at the first position with the first mode;

d) aligning the acquired output to the design data;

e) altering the values for the one or more parameters of the inspection system to a second mode different than the first mode;

f) without changing the position on the specimen to which the energy is directed and from which the energy is detected from the first position, acquiring the output generated by the detector at the first position with the second mode;

g) repeating steps e) and f) for one or more additional modes of the inspection system;

h) setting the values for the one or more parameters of the inspection system to the first mode;

i) controlling the scanning subsystem such that the position on the specimen to which the energy is directed and from which the energy is detected is a second position on the specimen at which a reference for the first position is formed;

j) acquiring the output generated by the detector at the second position with the first mode;

k) altering the values for the one or more parameters of the inspection system to the second mode;

l) without changing the position on the specimen to which the energy is directed and from which the energy is detected from the second position, acquiring the output generated by the detector at the second position with the second mode;

m) repeating steps k) and l) for the one or more additional modes of the inspection system;

n) repeating steps a) through g) for one or more additional positions on the specimen at which one or more additional known defects are located;

o) repeating steps h) through m) for one or more further positions on the specimen at which one or more references for the one or more additional positions are formed; and p) selecting one or more modes of the inspection system for inspection of the specimen or another specimen of the same type as the specimen based on all of the output generated by all of the steps of the computer-implemented method.

20. A method for selecting one or more modes of an inspection system for inspection of a specimen, comprising:

a) setting values for one or more parameters of the inspection system to a first mode known to generate output in which patterned features on the specimen are resolved to a degree that allows the output to be aligned to design data for the specimen, wherein the inspection system comprises at least an energy source, a detector, and a scanning subsystem, wherein the energy source is configured to generate energy that is directed to a specimen by the inspection system, wherein the detector is configured to detect energy from the specimen and to generate output responsive to the detected energy, wherein the scanning subsystem is configured to change a position on the specimen to which the energy is directed and from which the energy is detected, and wherein the scanning subsystem comprises a mechanical assembly configured to move the specimen and a stage on which the specimen is disposed;

b) controlling the scanning subsystem such that the position on the specimen to which the energy is directed and from which the energy is detected is a first position on the specimen at which a first known defect is located;

c) acquiring the output generated by the detector at the first position with the first mode;

d) aligning the acquired output to the design data;

e) altering the values for the one or more parameters of the inspection system to a second mode different than the first mode;

f) without changing the position on the specimen to which the energy is directed and from which the energy is detected from the first position, acquiring the output generated by the detector at the first position with the second mode;

g) repeating steps e) and f) for one or more additional modes of the inspection system;

h) setting the values for the one or more parameters of the inspection system to the first mode;

i) controlling the scanning subsystem such that the position on the specimen to which the energy is directed and from which the energy is detected is a second position on the specimen at which a reference for the first position is formed;

j) acquiring the output generated by the detector at the second position with the first mode;

k) altering the values for the one or more parameters of the inspection system to the second mode;

l) without changing the position on the specimen to which the energy is directed and from which the energy is detected from the second position, acquiring the output generated by the detector at the second position with the second mode;

m) repeating steps k) and l) for the one or more additional modes of the inspection system;

n) repeating steps a) through g) for one or more additional positions on the specimen at which one or more additional known defects are located;

o) repeating steps h) through m) for one or more further positions on the specimen at which one or more references for the one or more additional positions are formed; and p) selecting one or more modes of the inspection system for inspection of the specimen or another specimen of the same type as the specimen based on all of the output generated by all of the steps of the computer-implemented method, wherein steps a) through p) are performed by a computer system, and wherein the computer system is a device having one or more processors executing instructions from a memory medium.

* * * * *